(12) United States Patent
Kita et al.

(10) Patent No.: US 8,366,778 B2
(45) Date of Patent: Feb. 5, 2013

(54) BIOADHESIVE HYDROGELS

(75) Inventors: Kristin B. Kita, Conshohocken, PA (US); Nigel G. Smith, Norwich (GB); Anthony M. Lowman, Wallingford, PA (US); Garland W. Fussell, Thorndale, PA (US)

(73) Assignees: Synthes USA, LLC, West Chester, PA (US); Drexel University, Philadelphia, PA (US)

( * ) Notice: Subject to any disclaimer, the term of this patent is extended or adjusted under 35 U.S.C. 154(b) by 281 days.

(21) Appl. No.: 12/812,141

(22) PCT Filed: Jan. 12, 2009

(86) PCT No.: PCT/US2009/030731
§ 371 (c)(1),
(2), (4) Date: Jul. 8, 2010

(87) PCT Pub. No.: WO2009/089526
PCT Pub. Date: Jul. 16, 2009

(65) Prior Publication Data
US 2010/0286786 A1    Nov. 11, 2010

Related U.S. Application Data

(60) Provisional application No. 61/020,584, filed on Jan. 11, 2008.

(51) Int. Cl.
*A61F 2/44* (2006.01)
(52) U.S. Cl. .................. 623/17.16; 623/17.11
(58) Field of Classification Search .......... 606/246–249, 606/279; 623/17.11–17.16; 523/113, 114, 523/116, 118; 128/898
See application file for complete search history.

(56) References Cited

U.S. PATENT DOCUMENTS
2008/0076852 A1*  3/2008  Smith et al. .................. 523/115

FOREIGN PATENT DOCUMENTS
WO    2007067622    6/2007
WO    2008024771    2/2008

OTHER PUBLICATIONS

Int'l Search Report from copending appln. No. PCT/US2009/030731, dated Mar. 18, 2010.
Thomas, J, et al., "The effect of dehydration history on PVA/PVP hydrogels for nucleus pulposus replacement," Journal of Biomedical Materials Research, vol. 69, No. 2, May 15, 2004, pp. 135-140 (Abstract Only).

* cited by examiner

*Primary Examiner* — Eduardo C Robert
*Assistant Examiner* — Christina Negrellirodriguez
(74) *Attorney, Agent, or Firm* — Stradley Ronon Stevens & Young, LLP

(57) ABSTRACT

A method of forming and the resulting bioadhesive hydrogel composition for repairing or supplementing a nucleus pulposus of an intervertebral disc comprises at least a first component, a second component and a third component, wherein the first component, the second component and the third component are crosslinked. The first component comprises an amine-containing polymer component at a concentration from about 0.1% weight by weight to about 13.65% weight by weight. The second component comprises a hydrophilic polymer or pre-polymer component at a concentration from about 3% weight by weight to about 35% weight by weight. The third component comprises an aldehyde component at a concentration from about 0.1% weight by weight to about 30% weight by weight. A method of repairing or supplementing a nucleus pulposus of an intervertebral disc comprises implanting the bioadhesive hydrogel composition in a patient.

23 Claims, 14 Drawing Sheets

BIOADHESIVE HYDROGELS

CROSS-REFERENCE TO RELATED APPLICATIONS

This application is the National Stage of International Application No. PCT/US2009/030731, filed Jan. 12, 2009, which claims the benefit of U.S. Provisional Application No. 61/020,584, filed Jan. 11, 2008, the disclosures of which are incorporated herein by reference in their entireties for all purposes.

FIELD OF THE INVENTION

The present invention relates to a bioadhesive hydrogel composition, an apparatus and/or method for repairing or supplementing body tissue, including an intervertebral disc, and preferably to an apparatus and/or method for repairing or supplementing a nucleus pulposus of an intervertebral disc using a bioadhesive hydrogel composition.

BACKGROUND OF THE INVENTION

The human intervertebral disc is comprised of two major structures, an outer or peripheral tendinous structure, and an inner gelatinous nucleus pulposus located in a generally central region. Degeneration of the nucleus, typically associated with natural aging, may lead to disc degradation and loss of function.

Chronic back pain caused by injury or age-related degeneration of an intervertebral disc is a condition experienced by many patients. Current treatments range from bed rest to invasive surgical procedures, including spinal fusion and total disc replacement.

Replacement or supplementation of the nucleus pulposus can relieve pain, restore healthy physiologic function to the disc and/or prevent additional wear or deterioration of the annulus. Currently, few minimally invasive techniques exist for supplementation or replacement of the nucleus pulposus of a spinal disc into a selected site of a mammal. Even fewer techniques can provide the physiological/mechanical properties to restore the damaged disc to its full capacity.

Accordingly, it is desirable to provide a way for repairing a damaged intervertebral disc. Other objects and advantages of the present invention shall become apparent from the accompanying description and examples.

BRIEF SUMMARY OF THE INVENTION

The present invention relates to a bioadhesive hydrogel composition, an apparatus and/or method for repairing or supplementing an intervertebral disc and preferably to an apparatus and/or method for repairing or supplementing a nucleus pulposus of an intervertebral disc using a bioadhesive hydrogel composition.

One preferred embodiment of the present invention may comprise a bioadhesive hydrogel composition for repairing or supplementing a nucleus pulposus of an intervertebral disc comprising at least a first component, a second component and a third component, wherein the first component, the second component and the third component are crosslinked. The first component preferably comprises an amine-containing polymer component at a concentration from about 0.1% weight by weight to about 13.65% weight by weight. The second component preferably comprises a hydrophilic polymer or pre-polymer component at a concentration from about 3% weight by weight to about 35% weight by weight. The third component preferably comprises an aldehyde component at a concentration from about 0.1% weight by weight to about 30% weight by weight.

Another preferred embodiment of the present invention may comprise a bioadhesive hydrogel composition for repairing or supplementing a nucleus pulposus of an intervertebral disc comprising at least a first component, a second component and a third component. The first component preferably comprises an amine-containing polymer component selected from the group consisting of poly(ethylene imine), poly(diethyl aminoethyl methacrylate), poly(ethyl aminoethyl methacrylate), amine-grafted poly(vinyl alcohol) or amine-containing poly(ethylene glycol). The second component preferably comprises a hydrophilic polymer or pre-polymer component selected from the group consisting of poly(vinyl alcohol) and poly(ethylene glycol). The third component preferably comprises an aldehyde component selected from the group consisting of glutaraldehyde, poly(ethylene glycol)-dialdehyde, glyoxal, formaldehyde and malonaldehyde.

A further preferred embodiment of the present invention may comprise a bioadhesive hydrogel composition for repairing or supplementing a nucleus pulposus of an intervertebral disc comprising at least a first component, a second component and a third component, wherein the first component, the second component and the third component are crosslinked and the amine-containing polymer component and the aldehyde component are combined in such a way as to achieve about a one to one molar ratio of reactive amine groups to aldehyde groups. The first component comprises an amine-containing polymer component at a concentration from about 0.1% weight by weight to about 13.65% weight by weight. The second component comprises a hydrophilic polymer or pre-polymer component at a concentration from about 3% weight by weight to about 35% weight by weight. The third component comprises an aldehyde component at a concentration from about 0.1% weight by weight to about 30% weight by weight.

Another preferred embodiment of the present invention may comprise a kit for forming a bioadhesive hydrogel composition comprising at least one first container containing an amine-containing polymer component at a sufficient concentration to be injectable at room temperature or under operating room conditions; at least one second container containing a hydrophilic polymer or pre-polymer component at a sufficient concentration to be injectable at room temperature or under operating room conditions; and at least one third container containing an aldehyde component at a sufficient concentration to be injectable at room temperature or under operating room conditions, wherein when the aldehyde component, the amine-containing polymer component and the hydrophilic polymer or pre-polymer component are mixed the composition is crosslinked and contains about 0.1% weight by weight to about 13.65% weight by weight of the amine-containing component, about 3% weight by weight to about 35% weight by weight of hydrophilic polymer or pre-polymer component and about 0.1% weight by weight to about 30% weight by weight of aldehyde component.

A further preferred embodiment of the present invention may comprise a kit for forming a bioadhesive hydrogel composition comprising at least one first container containing a precursor composition comprising an amine-containing polymer component crosslinked to a hydrophilic polymer or pre-polymer component; and at least one second container loaded with an aldehyde component at a sufficient concentration to be injectable at room temperature or under operating room conditions, wherein when the aldehyde component, the amine-containing polymer component and the hydrophilic polymer or pre-polymer component are mixed the composition is crosslinked and contains about 0.1% weight by weight to about 13.65% weight by weight of the amine-containing component, about 3% weight by weight to about 35% weight by weight of hydrophilic polymer or pre-polymer component and about 0.1% weight by weight to about 30% weight by weight of aldehyde component.

An additional preferred embodiment of the present invention may comprise a method of repairing or supplementing a nucleus pulposus of an intervertebral disc comprising preparing the bioadhesive hydrogel composition comprising at least a first component, a second component and a third component, the first component comprising an amine-containing polymer component at a concentration from about 0.1% weight by weight to about 13.65% weight by weight, the second component comprising a hydrophilic polymer or pre-polymer component at a concentration from about 3% weight by weight to about 35% weight by weight, the third component comprising an aldehyde component at a concentration from about 0.1% weight by weight to about 30% weight by weight, wherein the first component, the second component and the third component are crosslinked; and implanting the composition into a patient.

BRIEF DESCRIPTION OF THE DRAWINGS

The foregoing summary, as well as the following detailed description of preferred embodiments of the application, will be better understood when read in conjunction with the appended drawings. The drawings, examples and embodiments described within this specification are to be understood as illustrative and exemplary of structures, features and aspects of the present invention and not as limiting the scope of the invention. It should be understood that the application is not limited to the precise arrangements and instrumentalities shown. In the drawings.

DETAILED DESCRIPTION OF THE INVENTION

Figure 1:
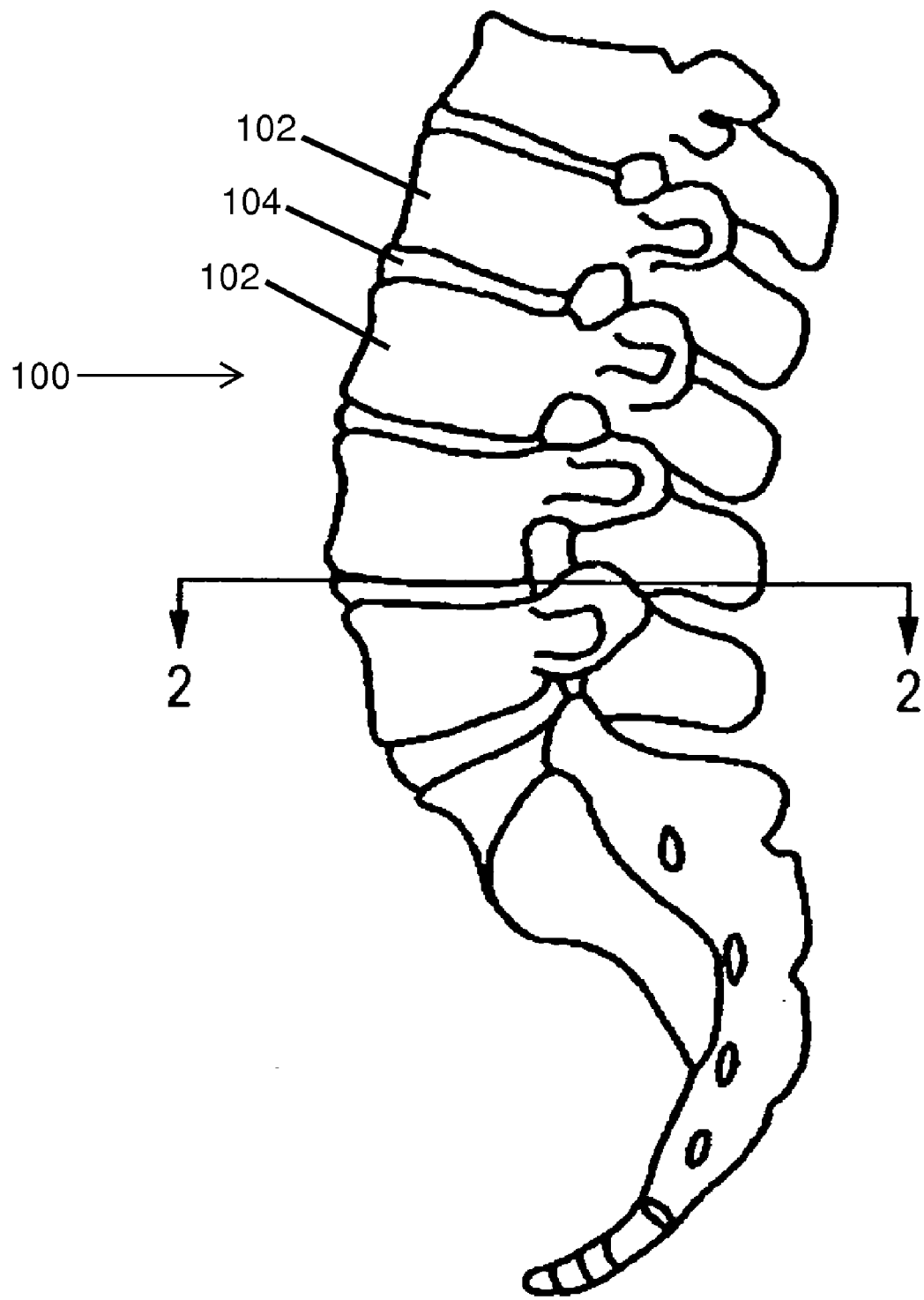
FIG. 1 is a schematic illustration of a portion of the human spinal column.

The methods, examples and embodiments described within this specification are to be understood as illustrative and exemplary of the composition, structures, features and aspects of the present invention and not as limiting the scope of the invention. Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior", "lateral" and related words and/or phrases designate preferred positions and orientations in the human body to which reference is made and are not meant to be limiting. All percentages, unless otherwise indicated, are on a weight by weight (w/w) basis. The terminology includes the above-listed words, derivatives thereof and words of similar import.

One preferred embodiment of the present invention may comprise a bioadhesive hydrogel composition for repairing a damaged intervertebral disc. The bioadhesive hydrogel composition may crosslink with its individual components as well as with surrounding tissue. The bioadhesive hydrogel composition may serve as a nucleus pulposus replacement or augmentation, as well as repairing defects, tears or fissures in the disc annulus.

The bioadhesive hydrogel composition may comprise at least three components and may form an injectable composition that may solidify in situ to form a hydrogel implant after being injected into tissues, including the intervertebral disc. The bioadhesive hydrogel composition may also comprise at least three components and may form a solid implant that may be inserted into the intervertebral disc. While one use for the composition described is for repairing or replacing a spinal disc, other uses for the composition are contemplated.

Figure 2:
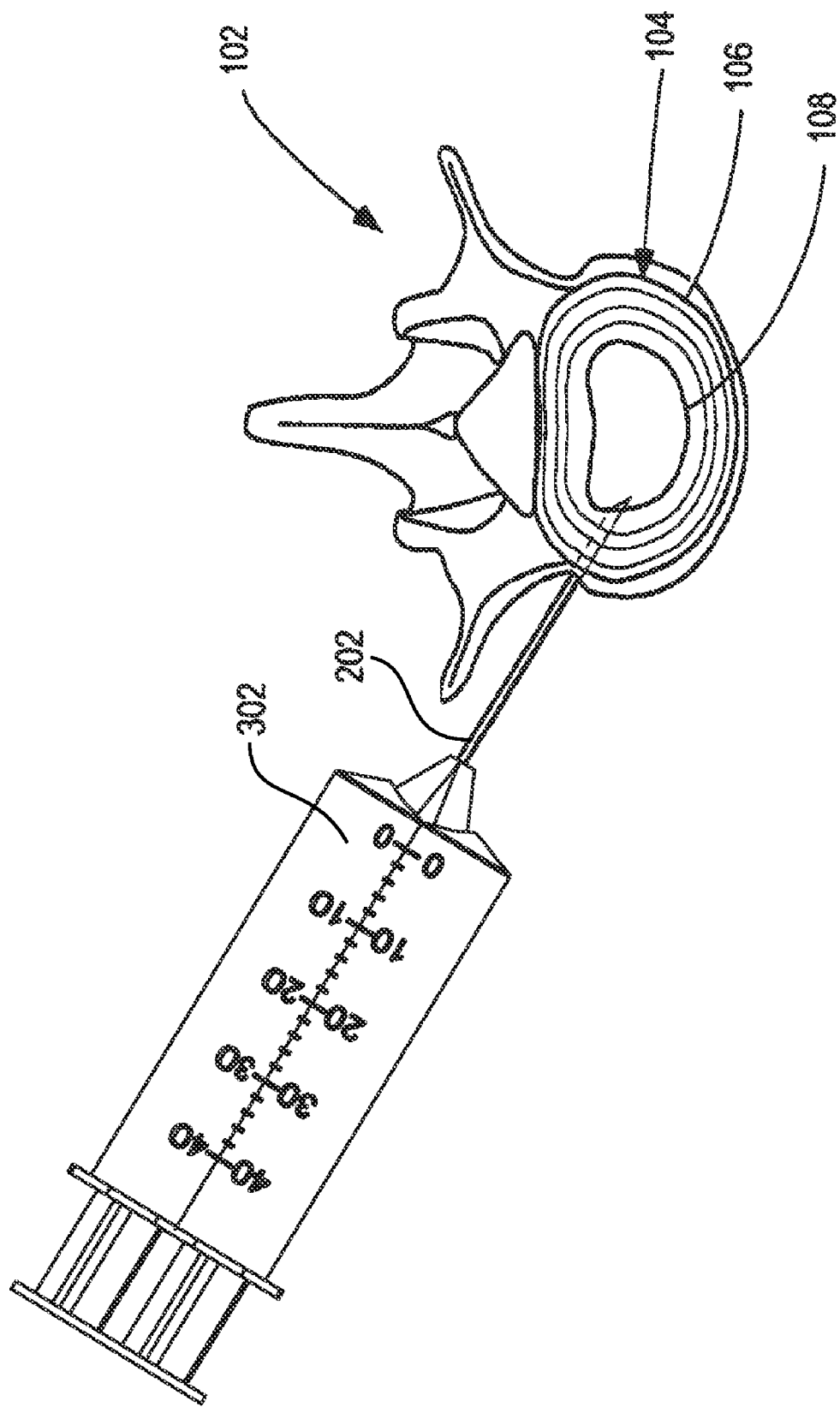
FIG. 2 schematically illustrates a first stage of implantation of an injectable bioadhesive hydrogel composition according to the present invention into a nucleus pulposus cavity according to the method of the invention, wherein a cannula, attached to a double barreled syringe, through which the bioadhesive hydrogel composition is to be implanted has been inserted through the annulus fibrosus of the intervertebral disc.
Figure 3:
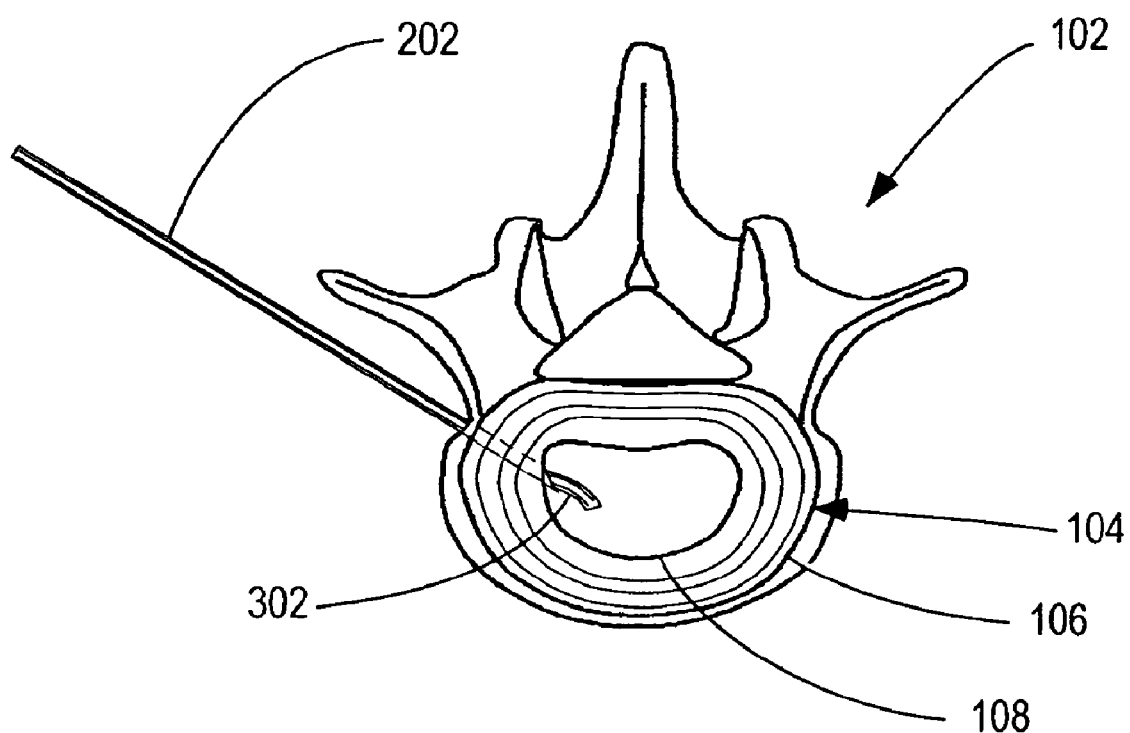
FIG. 3 schematically illustrates a second stage of the implantation, wherein extrusion of the bioadhesive hydrogel composition through the cannula into the cavity has begun.

An exemplary method of implantation of an injectable bioadhesive hydrogel composition according to the invention is illustrated schematically in FIGS. 1-3.

FIG. 1 illustrates a left lateral schematic view of the lumbar portion of a human spine 100, showing the general configuration of the vertebrae 102 and intervertebral discs 104. Although the invention will be described with respect to a lumbar intervertebral disc, a skilled practitioner will understand that it may be practiced with respect to any of the intervertebral discs, with appropriate modifications as may be appropriate.

The implantation of an injectable bioadhesive hydrogel composition according to the invention is illustrated in FIGS. 2 and 3, wherein the procedure is viewed from a superior view of a typical intervertebral disc as indicated by the line 2-2 in FIG. 1.

FIG. 2 shows the implantation of an injectable bioadhesive hydrogel composition according to the invention wherein a cannula 202 has been inserted though the annulus fibrosus 106 of an intervertebral disc 104 and into the nucleus pulposus cavity 108. The cannula 202 is shown attached to a double barreled syringe 302. The nucleus pulposus cavity 108 may be in need of a prosthesis by reason of natural degeneration or leakage of the nucleus pulposus or after partial or total removal of the natural nucleus pulposus. The cannula 102 may be any type of conventional cannula, including a cannula having a sharp point as illustrated or a blunt point, inserted through the annulus fibrosus 106 by any conventional surgical technique.

FIG. 3 shows an initial stage of the implantation wherein the extrusion of the injectable bioadhesive hydrogel composition from the cannula into the nucleus pulposus cavity has begun.

Hydrophilic gels, such as, for example, a PVA-containing gel, typically do not adhere to body tissue. The addition of an amine-containing polymer component and an aldehyde component preferably imparts tissue adhesive properties in vivo by enhancing the ability to integrate with surrounding tissues, resulting in a more physically stable implant that is less likely to be displaced due to biomechanical motions and forces. The bioadhesive hydrogel composition of the present invention preferably has a self-adhesion tensile strength between about sixty-five thousandths of a mega pascal (0.065 MPa) to about one mega pascal (1.0 MPa), more preferably between about eighty-five thousandths of a mega pascal (0.85 MPa) to about one-half of a mega pascal (0.500 MPa) and most preferably about one tenth of a mega pascal (0.100 MPa) to about twenty-five hundredths of a mega pascal (0.250 MPa).

Another preferred embodiment of the present invention may comprise a bioadhesive hydrogel composition comprising a first component, a second component and a third component; the first component comprising an amine-containing polymer component. The amine-containing polymer component may comprise poly (ethylene imine) (PEI), poly(diethyl aminoethyl methacrylate), poly(ethyl aminoethyl methacrylate), amine-grafted poly(vinyl alcohol) (amine-grafted PVA), or amine-containing poly(ethylene glycol) (amine-containing PEG). The amount of the amine-containing polymer component in the bioadhesive hydrogel composition may be from about one tenth of a percent (0.1%) (w/w) to about thirteen and sixty-five hundredths percent (13.65%) (w/w), preferably from about six tenths of a percent (0.6%) (w/w) to about ten and two tenths percent (10.2%) (w/w), more preferably from about seven percent (7.0%) (w/w) to about eight percent (8.0%) (w/w).

The second component of the bioadhesive hydrogel composition preferably comprises a hydrophilic polymer or pre-polymer component. The hydrophilic polymer or pre-polymer component preferably comprises poly(vinyl alcohol) (PVA) or poly(ethylene glycol) (PEG). The hydrophilic polymer or pre-polymer component is not limited to a specific molecular weight of polymer. The hydrophilic polymer or pre-polymer component, such as, for example, PVA, may impart hydrophilicity to achieve the desired hydrophilic properties that are similar to native nucleus pulposus tissue and connective tissues. The amount of the hydrophilic polymer or pre-polymer component in the bioadhesive hydrogel composition may be from about three percent (3%) (w/w) to about thirty-five percent (35%) (w/w), preferably from about eleven percent (11%) (w/w) to about twenty-three and three tenths percent (23.3%) (w/w) and more preferably from about fourteen and three tenths percent (14.3%) (w/w) to about fifteen percent (15%) (w/w).

The third component of the bioadhesive hydrogel composition preferably comprises an aldehyde component, preferably a poly-functional or di-functional aldehyde. The aldehyde component may comprise, glutaraldehyde, PEG-dialdehyde, glyoxal, formaldehyde and malonaldehyde. The addition of the aldehyde component may induce adhesion of the amine-containing polymer to the surrounding tissues, and/or increase the mechanical properties of the bioadhesive hydrogel composition by crosslinking the amine groups on the polymer. The amount of the aldehyde component in the bioadhesive hydrogel composition may be from about one tenth of a percent (0.1%) (w/w) to about thirty percent (30%) (w/w), preferably from about one and eight tenths percent (1.8%) (w/w) to about fifteen percent (15%) (w/w), more preferably from about two percent (2%) (w/w) to about ten percent (10%) (w/w). The remainder of the bioadhesive hydrogel composition may be water or other components and materials.

The bioadhesive hydrogel composition comprising the at least three components preferably provides for improved overall stability. The crosslinking of the aldehyde component with the amine groups and/or the hydrophilic polymer or pre-polymer component may create fully crosslinked network matrices where all of the components, other than water, may be crosslinked chemically with one another.

To form the bioadhesive hydrogel composition the amine-containing polymer component and the hydrophilic polymer or pre-polymer component may be combined first to form a hydrogel precursor composition before adding the aldehyde component. When the bioadhesive hydrogel composition is formed in this manner, the aldehyde component may diffuse through the hydrogel precursor network to promote inter-chain crosslinking and/or adhesion between the hydrogel and surrounding tissues, if the hydrogel is in situ when the aldehyde component is added.

Alternatively, the bioadhesive hydrogel composition may be formed by combining together, simultaneously or near simultaneously, the liquid forms of the at least three components (i.e., combining the hydrophilic polymer or pre-polymer component, the aldehyde component and the amine-containing polymer component). When the bioadhesive hydrogel composition is formed in this manner, the amine groups from the amine-containing polymer component preferably reacts with the functional groups on the aldehyde component to form a stable network. Preferably, when the aldehyde component is added to the liquid form of the first two components (such as, for example, the PVA/PEI combination), then the hydrophilic polymer or pre-polymer component (such as, for example, PVA) may become trapped within the network resulted from the crosslinking between the amine groups and the aldehyde component, forming a solid hydrogel mass that has bioadhesive properties.

In preferred embodiments of the present invention where the at least three liquid components are combined, simultaneously or near simultaneously, the aldehyde component may also react with the hydrophilic polymer or pre-polymer component to form acetal linkages as shown below:

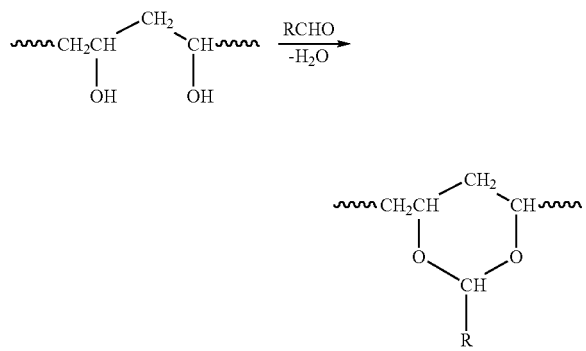

The reaction may occur spontaneously through acid catalysis. The reaction rates may be increased by reducing the pH to below 7.0. Thus, by controlling the pH, the reaction time may be lengthened or reduced. If desirable, the pH may be increased to temporarily prevent, or inhibit, such crosslinking between the hydrophilic polymer or pre-polymer component and the aldehyde component such that the combination of the components remains injectable. Maintaining injectability may be desirable when packaging the individual components in a kit form, such as, for example in a multi-chamber syringe or other delivery devices or containers.

In another preferred embodiment of the present invention the bioadhesive hydrogel composition may be formed by first blending, chemically coupling or copolymerizing the amine-containing polymer component with the hydrophilic polymer or pre-polymer component to form a precursor composition prior to the addition of the aldehyde component. The precursor composition may exist in a liquid (i.e., solution) state or in a solid (i.e., hydrogel) form. The particular phase may depend on the temperature and the concentration of each of the hydrophilic polymer or pre-polymer component with the amine-containing polymer component in the precursor composition. The resulting precursor composition, whether liquid or solid, then may react with the aldehyde component to form the bioadhesive hydrogel composition.

In another preferred embodiment of the present invention a hydrogel precursor composition comprising a hydrophilic polymer or pre-polymer component, such as, for example, a PVA hydrogel, may be formed via a physical crosslinking method, such as, for example, a cryogelation process that consists of repeatedly freezing and thawing a PVA-containing aqueous solution until a stable hydrogel is formed and improvements in mechanical properties are obtained. Other methods of physical crosslinking may include, but are not limited to, dehydration processing, exposure to radiation, or mixing of the components in the manner of Theta gels (i.e., preparation of a stable gel formulation by competitively removing excess solvent (e.g., water) using a further component which has a higher affinity for the solvent than the hydrogel component). PEI, or other amine-containing polymer component, may be incorporated in the PVA hydrogel by mixing or blending the PEI, or other amine-containing polymer component, in with the PVA solution prior to cryogelation. The PEI, or other amine-containing polymer component, may later react with the aldehyde component to increase the mechanical strength of the resulting bioadhesive hydrogel composition.

In another preferred embodiment of the present invention a hydrogel precursor composition may be formed by chemically coupling a hydrophilic polymer or pre-polymer component, such as, for example, PVA, to PEI or other amine-containing polymer component. PVA may be coupled to PEI, or another amine-containing polymer component, by forming an NHS-ester linkage between amines on PEI, or another amine-containing polymer component, and the hydroxyl functional groups on PVA. N,N'-Carbonyl diimidazole may be used to form N-alkyl carbamate linkages. The following chemical reaction shows the coupling of alcohols with amines through use of N,N'-Carbonyl diimidazole:

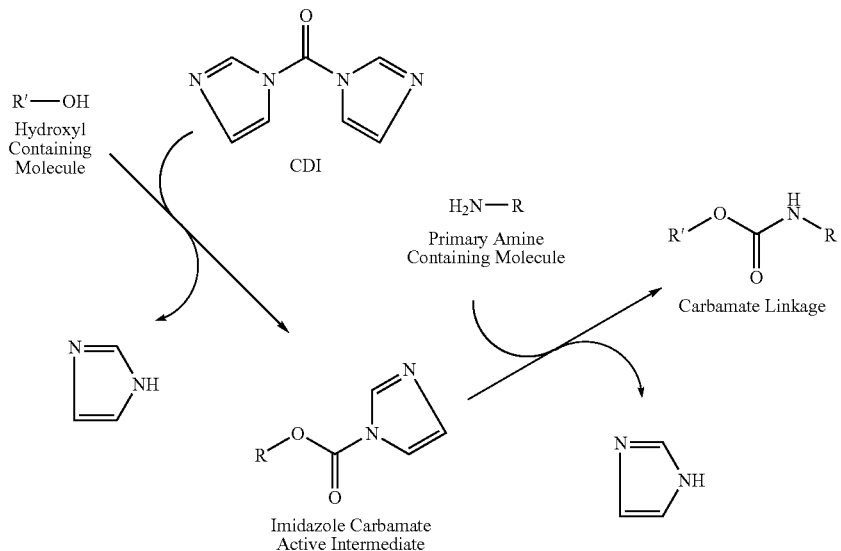

In another preferred embodiment of the present invention, disuccinic amidyl carbonate, another coupling agent, may be used to form similar linkages. The following chemical reaction shows the coupling of alcohols with amines through use of disuccinic amidyl carbonate.

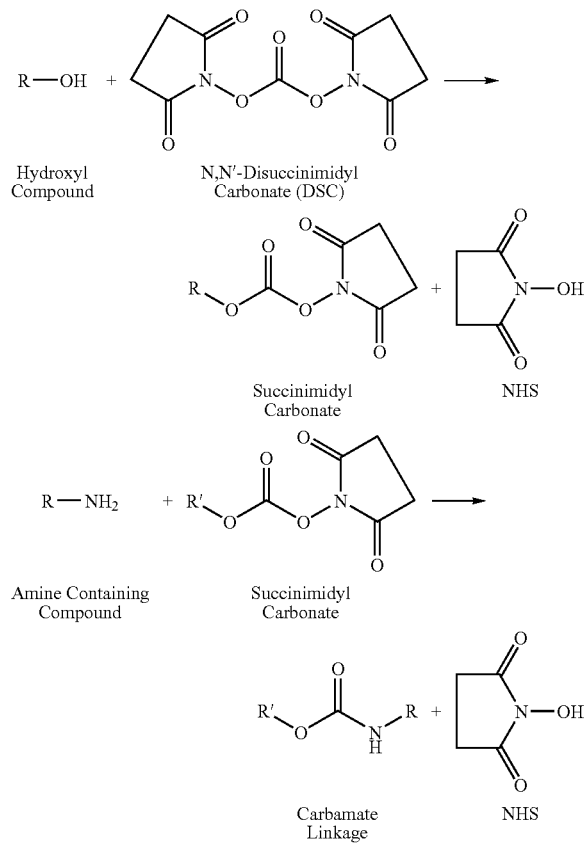

In another preferred embodiment of the present invention, the alcohols may be coupled to the amines through a two-step reaction. Succinic anhydride may be used to attach carboxylic acid groups to PVA for binding with amine groups of PEI via reactions with dicyclohexyl carbodiimide as described in the chemical reaction:

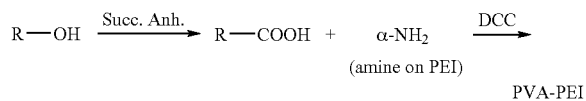

In the above preferred embodiment, α-$NH_2$ may be an amine group on the PEI molecule that when reacted with the carbonyl group on the PVA chain creates the PVA-PEI amide linkage.

The bioadhesive hydrogel composition comprising a combination of at least three of the above-described components may produce a cohesive solid or gelled substance. Polymeric components are not limited to a specific molecular weight of the polymers.

The bioadhesive hydrogel composition may be injectable and may be delivered via, for example, a dual or multi-barreled delivery and mix syringe (such as, for example, a Kenics static mixer) that can deliver the components concurrently or staged. Preferably, the bioadhesive hydrogel composition may remain injectable immediately after mixing but not after forty-eight hours.

One preferred embodiment of the present invention may comprise a bioadhesive hydrogel composition that is injectable and comprises about fourteen and eight tenths percent (14.7%) by weight of PVA, about seven and six tenths percent (7.6%) by weight of PEI, about six and seven tenths percent (6.6%) by weight of glutaraldehyde and about seventy and nine tenths percent (70.9%) of water.

Another preferred embodiment of the present invention may comprise a method of repairing and/or augmenting a damaged intervertebral disc comprising implanting a bioadhesive hydrogel composition comprising at the least three components described above.

EXAMPLES AND EXPERIMENTS

The following examples and experiments describe some of the properties of the preferred bioadhesive hydrogel composition described herein and are only intended to assist in explaining and illustrating the composition, structures, features and aspects of the bioadhesive hydrogel composition and not as limiting the scope of the invention to the precise arrangements, compositions, properties or features described.

Example 1

Preparation of and Stability Testing of PVA/PEI Hydrogel Precursor Compositions

To demonstrate the properties of a PVA/PEI Hydrogel Precursor Compositions, PVA/PEI Hydrogel Precursor Composition samples were subjected to stability testing in solution at 37° C. A PVA/PEI Hydrogel Precursor Composition was formed by blending PVA with varying concentrations of PEI (0.1%, 0.6% and 0.8%) and subjecting the resulting solution to cyrogelation as described above. The total polymer (i.e., combined PVA and PEI) concentration in this example is 10%. Thus, a percentage by weight designation of 0.1% PEI, for example, means that the composition was made up of 90% water and 9.9% PVA and 0.1% PEI.

To ensure that PEI trapped in a PVA-based hydrogel remains stable over a period of time after the sample has fully cured, the PVA/PEI Hydrogel Precursor Compositions were immersed in deionized water and removed at 0, 15, 45 and 60 days. The PVA/PEI Hydrogel Precursor Composition samples were then removed and freeze-dried.

Figure 4:
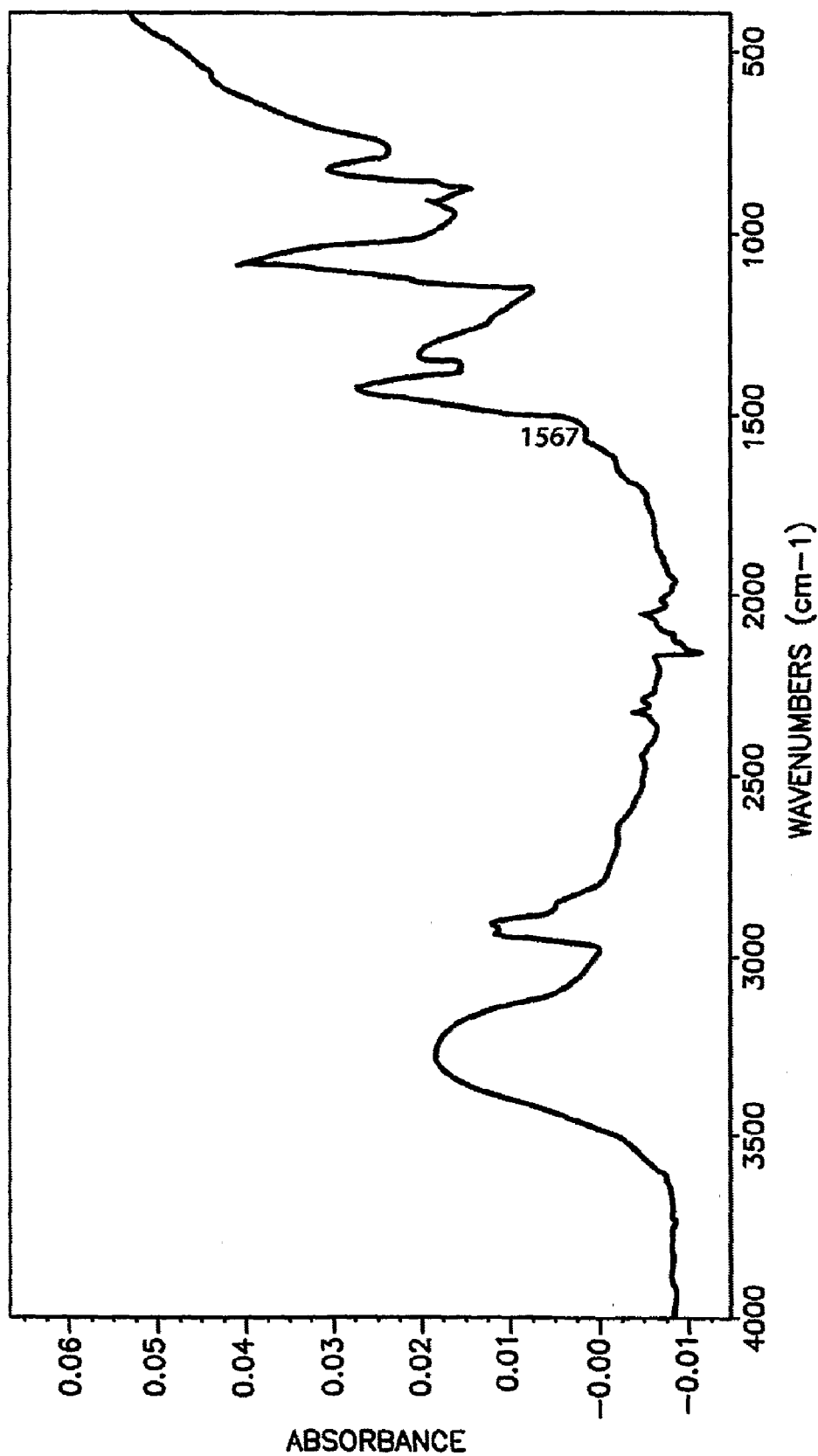
FIG. 4 is a FT-IR spectrum analysis of a PVA/PEI precursor composition before immersion (i.e., 0 days immersion)
Figure 5:
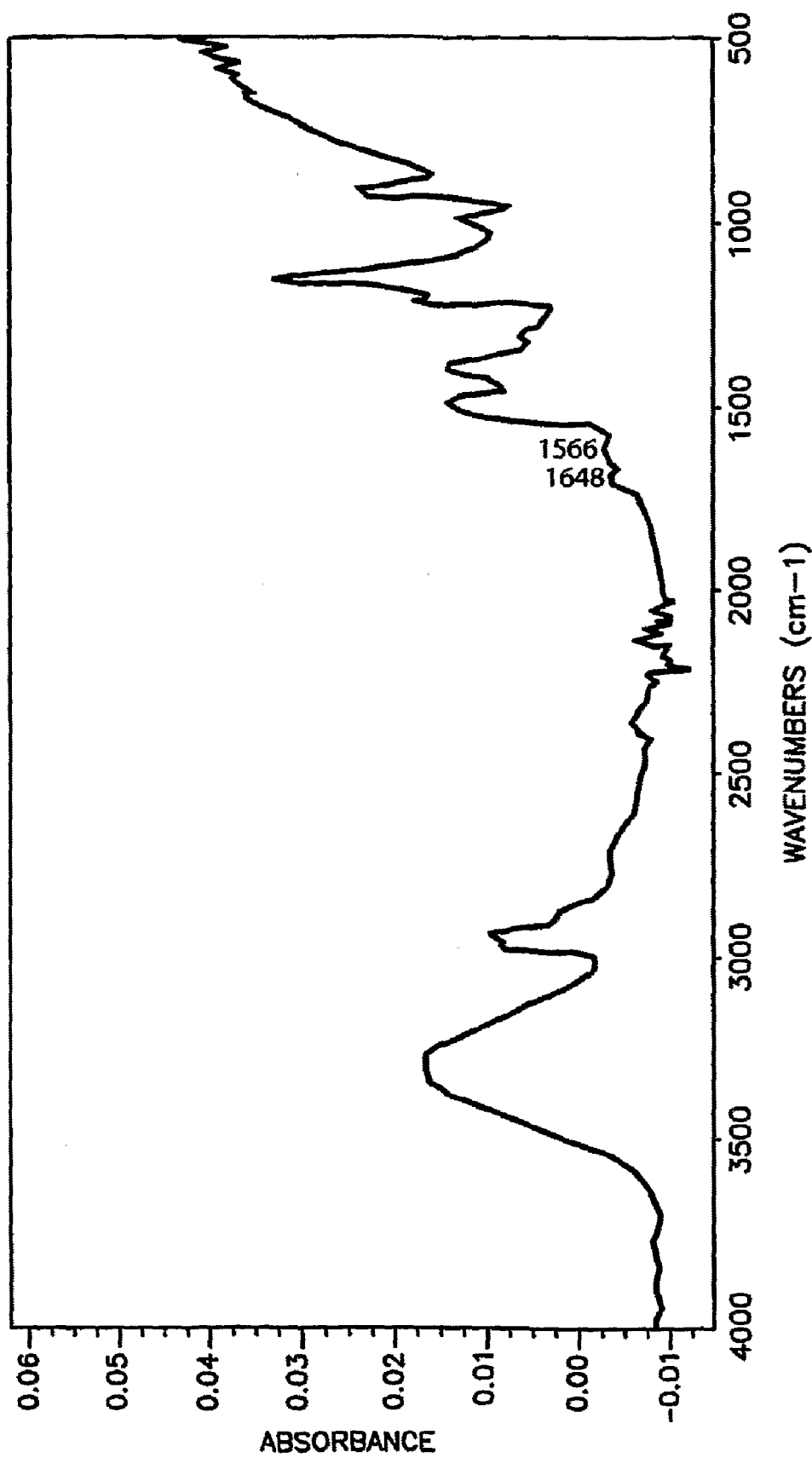
FIG. 5 is FTIR spectrum analysis of a PVA/PEI precursor composition following 60 days immersion.
Figure 6:
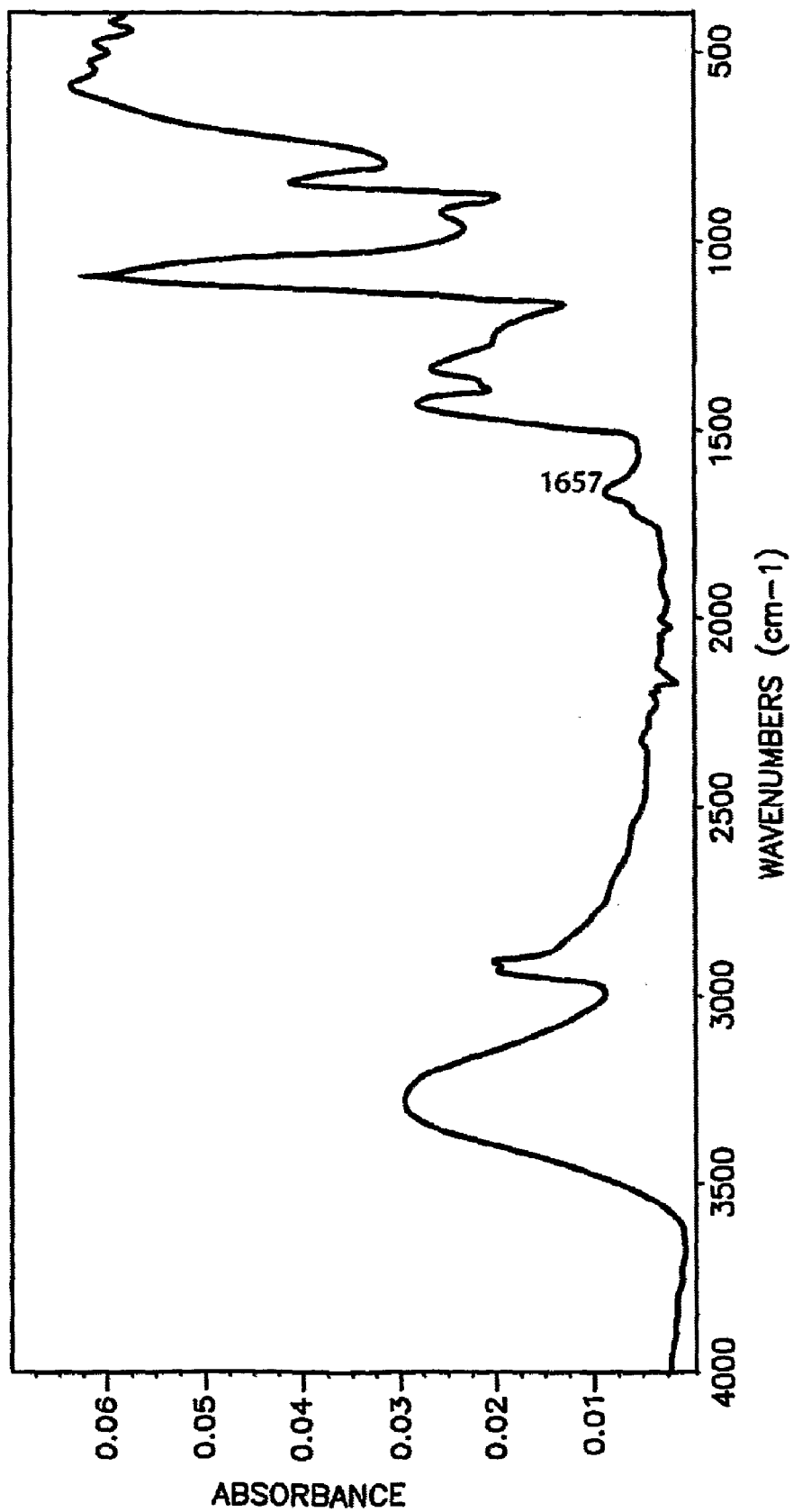
FIG. 6 is a FTIR spectrum analysis of a control sample (i.e., without PEI) at 0 days.

Each PVA/PEI Hydrogel Precursor Composition sample was then analyzed via Fourier transform spectroscopy (FT-IR) for the presence of the PEI. FT-IR measures chemical bond changes. The presence of the imine peak evidences that the PEI was stable and present. Representative results for the PVA/PEI Precursor Composition containing 0.8% PEI are shown in FIGS. 4-6. FIG. 4 shows the imine peak (circled in the figure) from PEI at 0 days immersion (1567 $cm^{-1}$). FIG. 5 shows the presence of the same imine peak (circled in the figure) remaining after a 60 day immersion (1566 $cm^{-1}$), evidencing that PEI of a molecular weight of 60 kDa remained in the gels for the full 60-day stability period. Comparatively, FIG. 6 shows the FT-IR of a control PVA/polyvinyl pyrrolidone (PVP) sample with no visible peak (circled in the figure) in the 1560 $cm^{-1}$ range.

Example 2

Compressive Mechanical Testing of PVA/PEI Hydrogel Precursor Compositions

To test the mechanical strength of a PVA/PEI Hydrogel Precursor Composition, sample hydrogel precursor compositions containing varying percentages by weight of PEI, ranging from 0.1% to 0.8% were prepared as described above and allowed to cure for seventeen hours. Control PVA/PVP hydrogel samples containing 0.1% PVP percentage by weight were also prepared. The total polymer (i.e., for example, combined PVA and PEI) concentration in this example is 10%. Thus, a percentage by weight designation of 0.1% PEI, for example, means that the composition was made up of 90% water and 9.9% PVA and 0.1% PEI.

Figure 7:
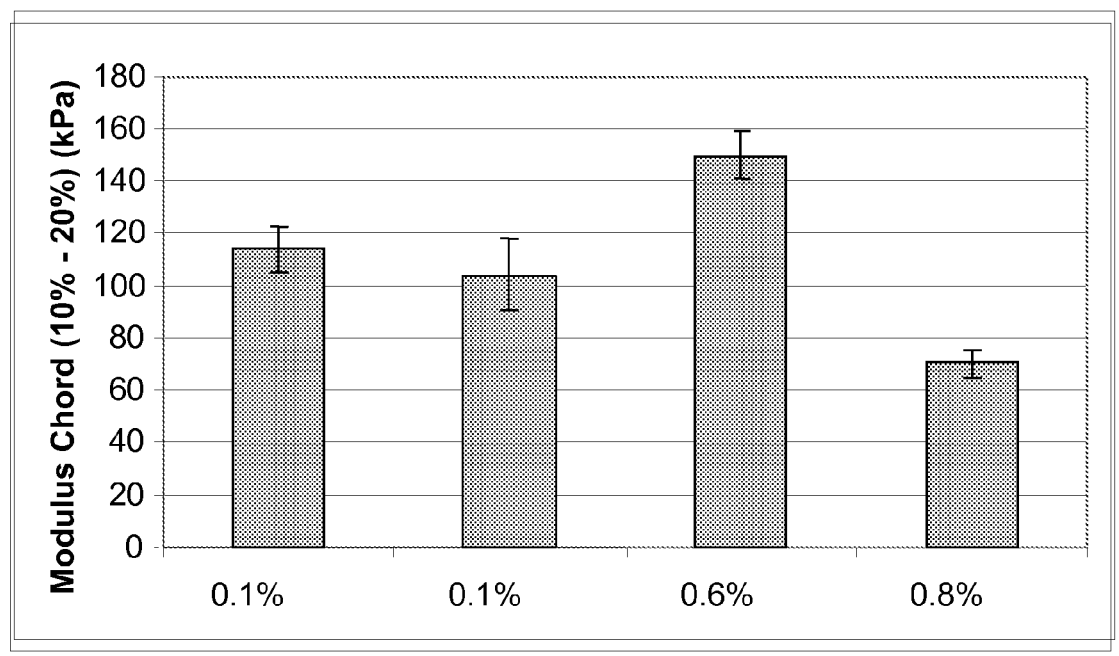
FIG. 7 is a graphical representation of the compressive mechanical properties of PVA/PEI Precursor Compositions equilibrated in deionized water.

The resulting PVA/PEI Hydrogel Precursor Compositions and control samples were formed into cylinders. All the sample cylinders (Control and PVA/PEI Hydrogel Precursor Compositions) measuring twelve millimeters (12 mm) in diameter and eight millimeters (8 mm) in height were first equilibrated in deionized water to achieve constant mass, then mechanically tested to determine the amount of compressive stress the samples can withstand before the samples begin to deform under crushing load. The results from the testing of compressive modulus at 10-20% strain are shown in FIG. 7. As shown in FIG. 7, PVA/PEI Precursor Hydrogel Compositions having 0.6% percentage by weight of PEI had a compressive modulus of more than one hundred forty kilopascals (140 kPa), greater than the control PVA/PVP sample, while PVA/PEI Precursor Hydrogel Compositions containing 0.1% PEI and 0.8% PEI, respectively, both show less mechanical strength than the control PVA/PVP sample.

Example 3

Compressive Mechanical Testing of PVA/PEI Precursor Hydrogel Compositions Following Pre-Conditioning in PEI PVA/PEI Precursor Hydrogel Compositions and control PVA/PVP hydrogel samples were prepared via cryogelation as described in Example 1 and 2, respectively. The cryogels were pre-conditioned (i.e., soaked) in PEI solution, to increase the available amine moieties for reaction. The ratio between the volume of the PEI solution and the volume of the cryogel samples was greater than 5 to 1.

Figure 8:
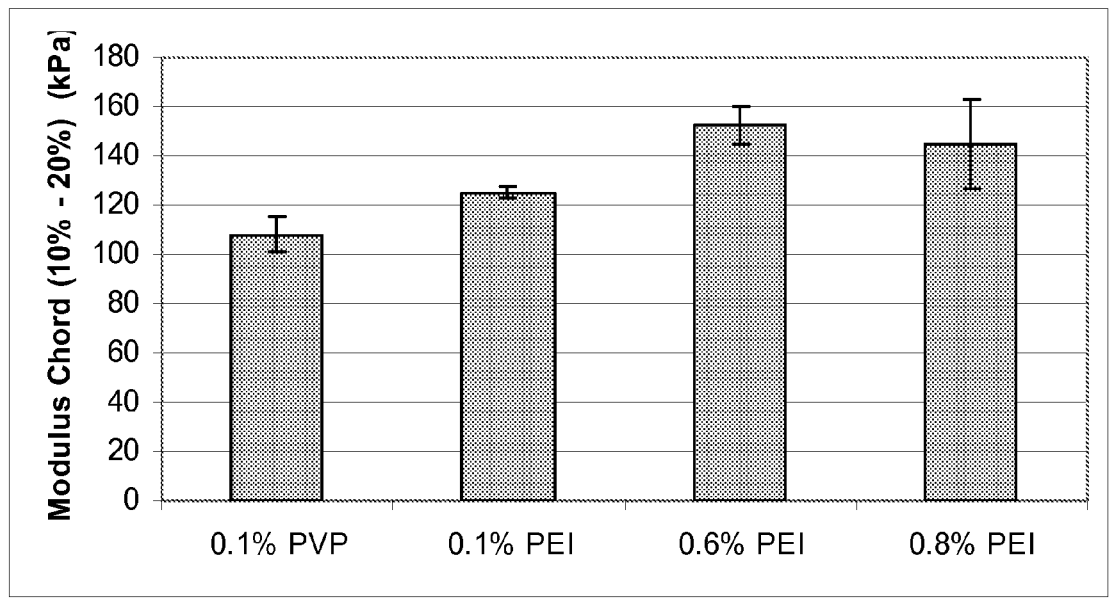
FIG. 8 is a graphical representation of the compressive mechanical properties of PVA/PEI Precursor Compositions equilibrated in an aqueous PEI solution.

In order to see the effect of pre-conditioning in PEI solution compared to those samples that were equilibrated in deionized water, twelve millimeters (12 mm) diameter×eight millimeters (8 mm) height cylindrical samples (n=7 for each formulation) containing different percentages by weight of PEI ranging from 0.1% to 0.8% pre-conditioned in a 2% aqueous PEI solution were used. The total polymer (i.e., for example, combined PVA and PEI) concentration in this example is 10%. Thus, a percentage by weight designation of 0.1% PEI, for example, means that the composition was made up of 90% water and 9.9% PVA and 0.1% PEI. FIG. 8 summarizes the results of the compressive mechanical analysis of PVA/PEI Precursor Compositions pre-conditioned in aqueous PEI solution at 10-20% strain. As demonstrated by comparing FIG. 7 to FIG. 8, all PVA/PEI Precursor Hydrogel Compositions pre-conditioned in an aqueous PEI solution were able to withstand greater compression than the PVA/PEI Hydrogel Precursor Compositions pre-conditioned in deionized water, with the most significant increase in strength seen in the 0.1% and 0.8% PEI samples. The 0.6% PEI sample pre-conditioned in a PEI solution exhibited similar compressive strength as the 0.6% PEI sample pre-conditioned in deionized water. The PVA/PEI Hydrogel Precursor Compositions pre-conditioned in PEI solution had greater compressive strength than the control PVA/PVP hydrogel samples.

Example 4

Self Adhesion Test of the Bioadhesive Hydrogel Composition

In order to determine the self-adhesive properties of the Bioadhesive Hydrogel Composition when an aldehyde component (in this example, a dialdehyde) was applied to a PVA/PEI Hydrogel Precursor Composition, a butt joint (i.e., axial) tensile adhesion test was performed on an Instron Mechanical Testing System (Model No. 3342) using the same size (i.e., 8 mm height×12 mm diameter) PVA/PEI Precursor Hydrogel Composition or control PVA/PVP hydrogel sample cylinders. PVA/PEI Precursor Hydrogel Compositions and control PVA/PVP samples were prepared via cryogelation as described above in Examples 1 and 2, respectively. The total polymer (i.e., for example, combined PVA and PEI) concentration in this example is 10%. Thus, a percentage by weight designation of 0.1% PEI, for example, means that the composition was made up of 90% water and 9.9% PVA and 0.1% PEI. Seven sample cylinders for each of the PVA/PEI Precursor Hydrogel Composition or control PVA/PVP hydrogel sample cylinders were analyzed. The sample cylinders were first glued using cyanoacrylate to the upper and lower steel plate of the Instron Mechanical Testing System. Sample cylinders were then bisected and 10% glutaraldehyde solution was applied to the cylinders using a syringe to the separate surfaces on each sample cylinder. Sample cylinders were then pressed together using a one Newton (1 N) preload for ten minutes at ambient temperature. The adjacent surfaces of the sample cylinder with the glutaraldehyde solution changed color to a reddish orange which is indicative of the aldehyde/amine reaction. The sample cylinders were then tested in tension to determine how much force the butt joint could withstand before adhesive failure at the bisection joint.

Table 1 summarizes the tensile strength data of the results from the seven sample cylinders from each group.

TABLE 1

Self-Adhesion Data for the Sample Cylinders

| | Average Tensile Strength (mega pascals ((MPa)) | Standard Deviation (MPa) |
|---|---|---|
| PVA/PVP (0.1% PVP) | 0.049 | ±0.017 |
| PVA/PEI (0.6% PEI) | 0.090 | ±0.018 |
| PVA/PEI (0.8% PEI) | 0.083 | ±0.041 |

As can be seen, samples with 0.6% PEI and 0.8% PEI show significantly higher tensile strength than the control PVA/PVP sample cylinders.

Example 5

Self Adhesion Test of Pre-Conditioned Bioadhesive Hydrogel Composition

Seven sample cylinders for each of the PVA/PEI Hydrogel Precursor Composition or control PVA/PVP hydrogel sample cylinders were analyzed as described in Example 4. However, the sample cylinders in this example were pre-conditioned in 18.25% PEI solution (the balance being water) before applying the 10% glutaraldehyde solution.

Table 2 below summarizes the tensile strength data.

TABLE 2

Self-Adhesion Data for the Pre-Conditioned Sample Cylinders

|  | Average Tensile Strength (MPa) | Standard Deviation (MPa) |
|---|---|---|
| PVA/PVP (0.1% PVP) | 0.064 | ±0.031 |
| PVA/PEI (0.1% PEI) | 0.112 | ±0.059 |
| PVA/PEI (0.6% PEI) | 0.103 | ±0.017 |
| PVA/PEI (0.8% PEI) | 0.126 | ±0.029 |

While all of the sample cylinders demonstrated an increased average tensile strength, PVA/PEI samples containing 0.8% PEI showed the best result, obtaining an average tensile strength of 0.126 MPa, almost doubling the tensile strength of the control PVA/PVP sample.

Example 6

Tissue Adhesion Test

Figure 9:
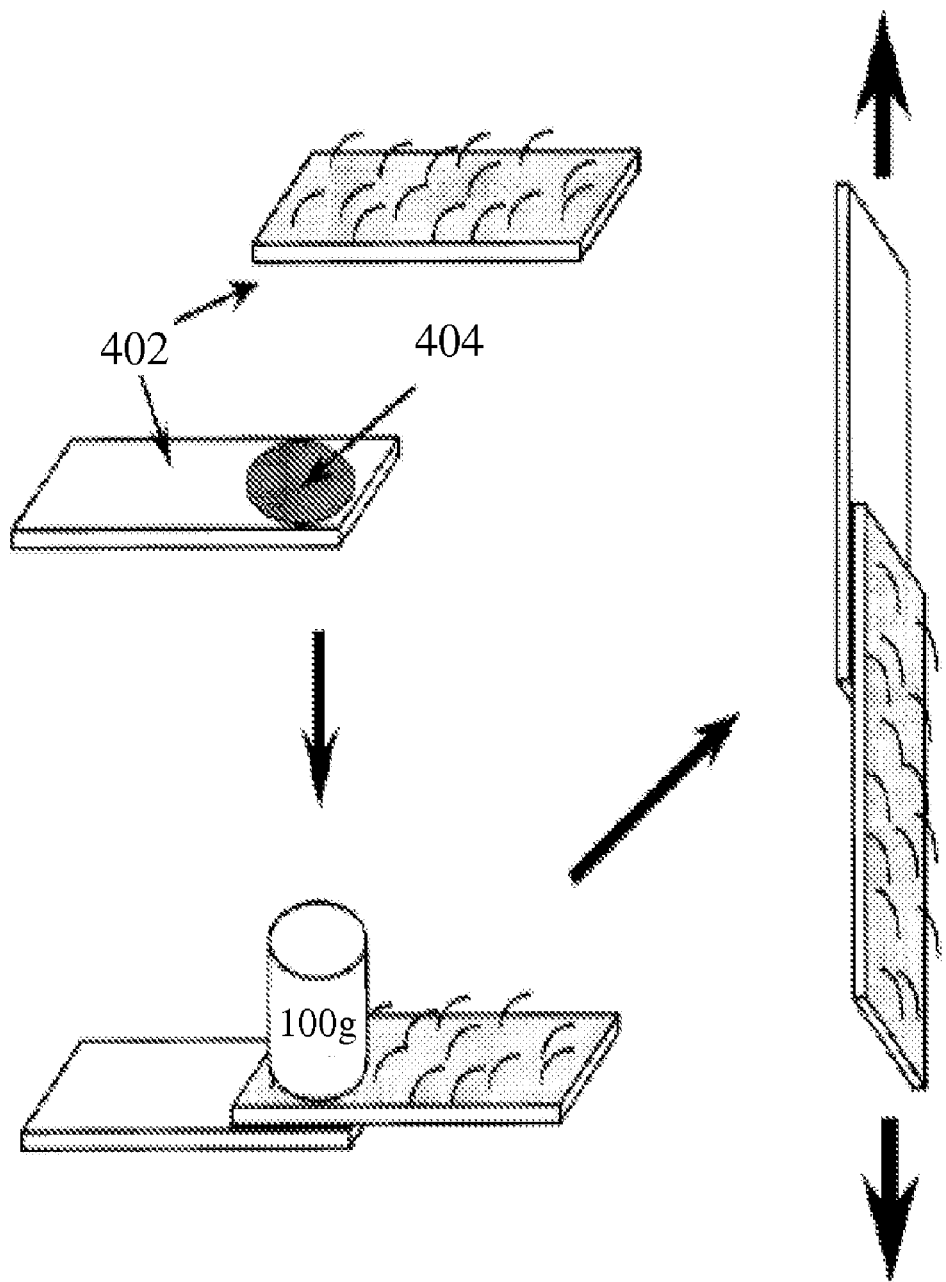
FIG. 9 is a schematic for lap joint sample preparation and testing.

To determine tissue adhesion properties of the Bioadhesive Hydrogel Composition, PVA/PEI Hydrogel Precursor Compositions were prepared via cryogelation as described above in Example 1. Low profile cylinders (i.e., short and wide, like, for example, a coin) of the PVA/PEI Precursor Compositions 404 were cut and sandwiched between two overlapping pieces of porcine skin 402. After applying aldehyde to the sample cylinders, the sample cylinders were placed under a one hundred gram (100 g) weight for two hours to allow for adhesion to occur. A lap joint sample was made using the process depicted in FIG. 9, then tested for adhesion strength by pulling the adhered pieces in opposite directions according to the lap shear adhesion test method provided in ASTM D1002-05.

Figure 10:
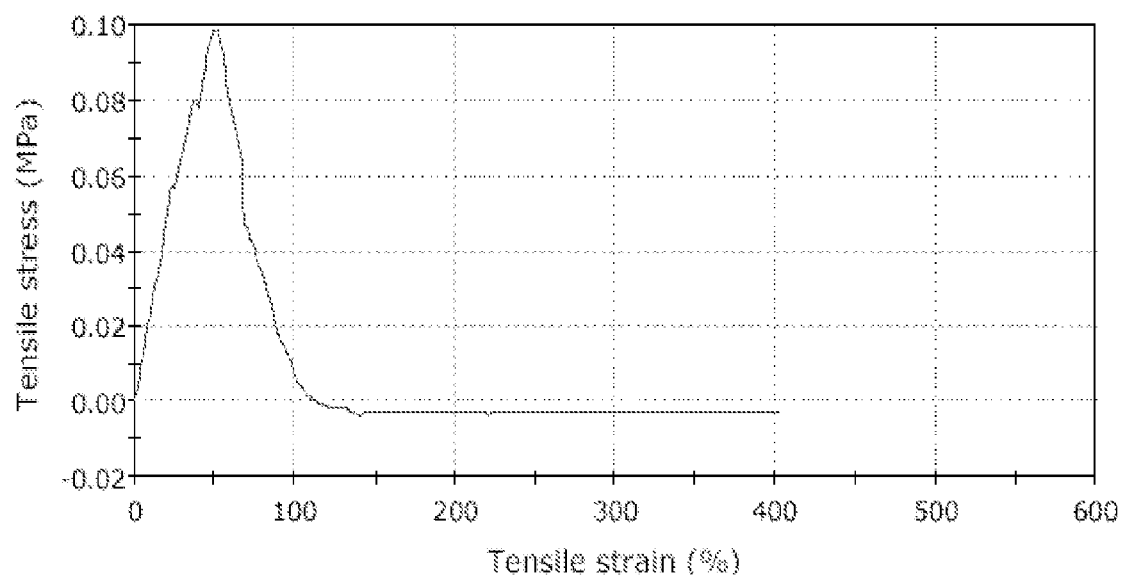
FIG. 10 is a graphical representation of the adhesion strength of a PVA/PEI Precursor Composition equilibrated in an aqueous PEI solution.

FIG. 10 shows a representative curve of a shear stress test at peak machine load using a PVA/PEI Hydrogel Precursor Composition sample cylinder having 0.6% w/w PEI that was pre-conditioned in a 6.25% PEI solution (the balance being water). The top of the curve (i.e., 0.10 MPa) represents the adhesive strength of the sample cylinder being tested. Three concentrations of PEI solutions, 6.35%, 12.5% and 18.25%, were also evaluated to determine the effect on tissue adhesion when the sample cylinders were pre-conditioned in varying PEI solutions. It was determined that sample cylinders pre-conditioned in 18.25% w/w PEI solution showed the highest adhesive strength.

Example 7

Preparation of a Co-Injectable PVA/PEI Hydrogel Composition

An injectable Bioadhesive Hydrogel Composition was prepared using a 2 to 1 volume ratio between a solution of PVA and PEI (referred to as Component A in this example) and glutaraldehyl (referred to as Component B in this example) as depicted in Table 3 (i.e., a 2:1 ratio of Component A to Component B). Formulations were chosen to enable reaction between all aldehyde and reactive amine functional groups (this is a 1:1 aldehyde to amine reaction). The calculations to derive the appropriate percentages of components to achieve 1:1 aldehyde to amine reaction and calculation of solution concentrations are described in more detail below.

TABLE 3

Bioadhesive Hydrogel Composition Component Solutions

| Ratio of aldehydes to amines | Component A | Component B |
|---|---|---|
| 1:1 | 11.45% w/v PEI 22.32% w/v PVA | 20% (w/v) glutaraldehyde |

To prepare Component A, 25% w/w Mowiol 28-99 PVA solution was made by weighing 25 grams of the granules into a media storage bottle followed by 75 grams of water. The bottle was capped and placed into an oven at 95° C. A 25% PVA solution was chosen because it was approximately the highest concentration that could be prepared in water without any visible separation (i.e., undissolved material remaining in the bottle). After the PVA had dissolved completely, the bottle was transferred and maintained in a 75° C. water bath. Elevated temperatures are not a requirement of the system, but may be utilized to facilitate injection of components that would otherwise be too viscous to inject at room temperature. 11.45 grams of PEI was weighed into a vessel and the PVA solution was added to bring the final volume to 100 ml.

To prepare Component B, 70% glutaraldehyde was diluted to 20% w/v solution using the appropriate amount of distilled water.

Component A and Component B were mixed, transferred to molds where they were allowed to cool to room temperature, and allowed to solidify through the spontaneous thermodynamic process of PVA gelation, as well as through the glutaraldehyde/PEI crosslinking reaction. A secondary, slower PVA/glutaraldehyde reaction has also been observed to occur between PVA and glutaraldehyde spontaneously at a pH of 7.0. The composition of an example of a Bioadhesive Hydrogel Composition is summarized in Table 4 as a mass percentage.

TABLE 4

Co-Injectable Bioadhesive Hydrogel Composition.

| Material | Composition (% w/w) |
|---|---|
| PVA | 14.7% |
| PEI | 7.6% |
| Water | 70.9% |
| Glutaraldehyde | 6.6% |

Calculations

PEI that is produced in a highly branched form has been shown to have a ratio of primary to secondary to tertiary amines of 1:2:1 (i.e., each molecule has 25% primary, 50% secondary, and 25% tertiary amines). Typical reaction schemes are two acid-catalyzed nucleophilic addition reactions of primary and secondary amines to aldehydes.

As a result of synthesis of PEI, primary amines constitute repeat units of —$CH_2CH_2NH_2$, secondary amine repeat units are —$CH_2CH_2NH$—, and tertiary amine repeat units are $CH_2CH_2N$ with respective molar masses of 44 g/mol, 43 g/mol, 42 g/mol. Based on a total molecular mass of 10,000 g/mol composed of ideal repeat units, each consisting of one primary amine unit, two secondary amine units and one tertiary amine unit, the sum of this repeat group is 172 grams/mole. Therefore, 10,000/172=58.14 is the number of these composite repeat units per molecule.

Since there are 58.14 composite repeat groups per molecule, it follows that per mole of PEI there are 58.14 moles of primary amines, 116.28 moles of secondary amines, and 58.14 moles of tertiary amines. This translates to 5.814, 11.628, 5.814 milli-moles each of primary, secondary and tertiary amines, respectively, per gram of PEI. Since only primary and secondary amines react, the moles of tertiary amines are discounted and therefore 17.442 mmol of reactive amines (5.813 for primary+11.628 for secondary) are available per gram of PEI.

Glutaraldehyde is 100.117 g/mol. There are two available aldehydes per molecule, so $2*1/(100.117*10^{-3}$ g/mmol) =19.98 milli-moles of aldehydes per gram.

A stoichiometric reaction (1:1 molar) between aldehyde and amine groups is desirable. Component solutions have been prepared as grams of substance per unit volume, so an accurate amount of reactive substance would be known per volume delivered.

To increase the polymer content, elasticity, and hydrophilicity of the product, a PVA solution was mixed with the PEI component. The final solution was then 11.455+/−0.1 g of PEI brought to a final volume of 100+/−0.1 ml by adding PVA solution. The concentration of PVA solution that was used was chosen to be 25%, since it was the maximum amount of polymer that would form a flowable liquid solution. Higher percentages of PVA can be utilized and still provide flowable liquid solution suitable for injection if the temperature of the solution is increased. The temperature may be increased up to 50° C. Injection of solution with temperature higher than 50° C. may cause damage to the surrounding tissues. Alternatively, without increasing the temperature, a delivery method that can deliver a more viscous solution may be used.

In this example, 1 ml of glutaraldehyde solution (20% w/v; 1.0 ml, 3.996 mmol) and 2 ml PEI (10,000 g/mol) solution (11.46% w/v; 1.0 ml, 1.998 mmol) were mixed to yield the stoichiometric (1:1 molar) reaction.

It should be noted that the formulation is not limited to the one described above. Any combination of the above components preferably producing a cohesive solid or gelled substance is desirable. Polymeric components PEI and/or PVA may be of different molecular weights than used (or isomers). PVA may have any percentage hydrolysis (percentage conversion of acetate to hydroxyl groups) that preferably yields hydrophilic properties within the Bioadhesive Hydrogel Composition. Components may be further loaded into a delivery system. A non-limiting example of such a system would be a dual barreled syringe with a Kenics static mixer attachment at the syringe aperture.

Example 8

Compressive Mechanical Testing of Sample Bioadhesive Hydrogel Compositions

Figure 11:
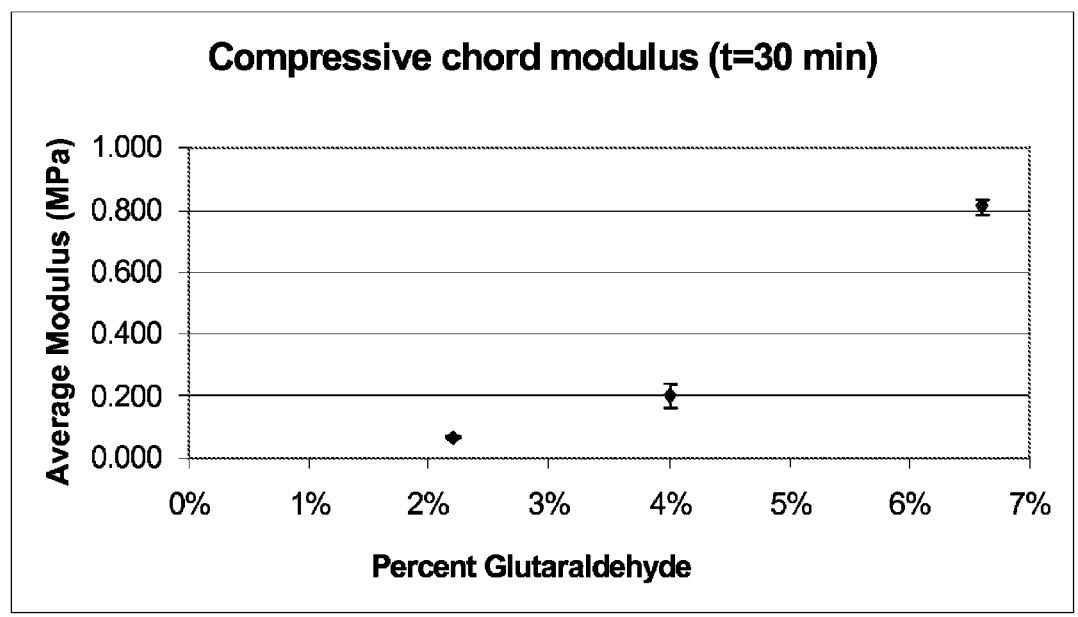
FIG. 11 is a graphical representation of the compressive mechanical properties of sample Bioadhesive Hydrogel Compositions at 15% strain at thirty minutes after molding.
Figure 12:
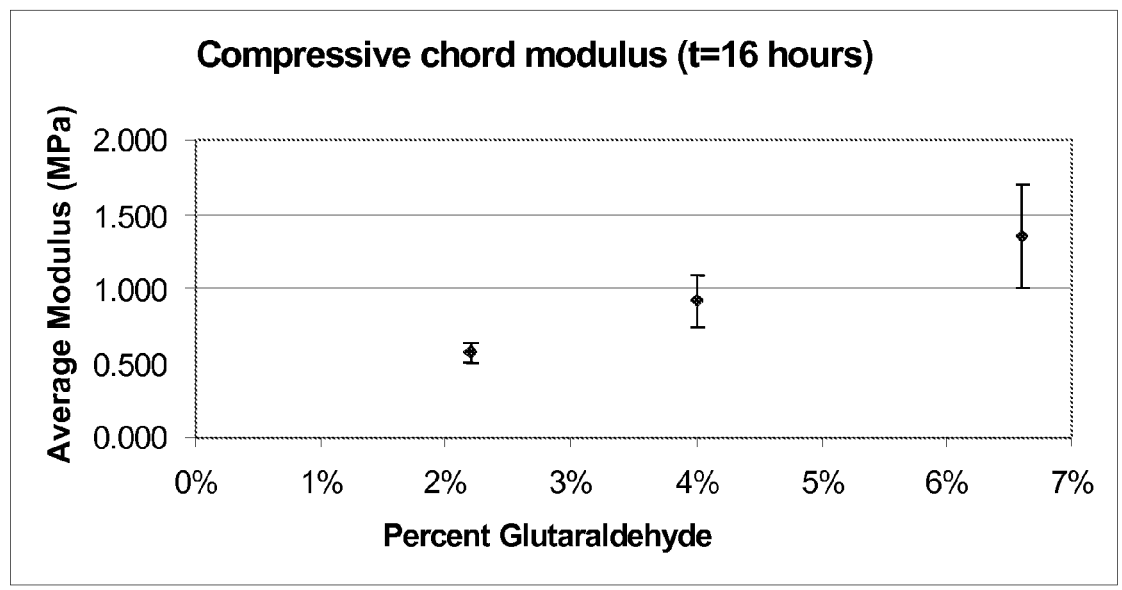
FIG. 12 is graphical representation of the compressive mechanical properties of sample Bioadhesive Hydrogel Compositions at 15% strain at sixteen hours after molding.

Sample Bioadhesive Hydrogel Compositions as prepared in Table 4 were tested after molding in axial compression to 35% strain on an Instron Mechanical Testing System (Model No. 3342). The sample Bioadhesive Hydrogel Compositions were cohesive and had solidified when tested. Compressive modulus of the sample Bioadhesive Hydrogel Compositions were tested thirty minutes after molding at 15% strain. This data is depicted in FIG. 11. Compressive modulus of the sample Bioadhesive Hydrogel Compositions were tested sixteen hours after molding at 15% strain. This data is depicted in FIG. 12. The values generated from this example are considerably higher than comparable hydrogel precursor compositions containing PVA and PEI or control PVA/PVP samples (i.e., without glutaraldehyde). Compare data from FIGS. 7 and 8.

Additional formulations of Bioadhesive Hydrogel Compositions with varying concentrations of glutaraldehyde were also prepared, as detailed in Table 5, and analyzed. The moduli of these materials at 15% strain were lower than the moduli of the 6.6% glutaraldehyde formulation at 30 minutes and 16 hours after molding (See FIGS. 8 and 9.) Additionally, the color change representative of the aldehyde/amine reaction was also noted. The color of the samples darkened over time such that the samples after sixteen hours of molding were a much deeper red color that the samples that had only been allowed to mold for thirty minutes.

TABLE 5

Example formulations of PVA-PEI with glutaraldehyde

| Formulation | PVA | PEI | Glutaraldehyde | Water |
|---|---|---|---|---|
| 1 | 14.7% | 7.6% | 6.6% | 71.0% |
| 2 | 17.7% | 9.1% | 4.0% | 69.2% |
| 3 | 19.7% | 10.2% | 2.2% | 68.0% |

Percentages on a weight by weight basis

Another formulation of Bioadhesive Hydrogel Compositions with a five percent glutaraldehyde concentration was prepared, as detailed in Table 6.

TABLE 6

Adhesion test formulation

| | Composition (% w/w) |
|---|---|
| PVA | 4.4% |
| PEI | 5.6% |
| Water | 84.9% |
| Glutaraldehyde | 5.0% |

Figure 13:
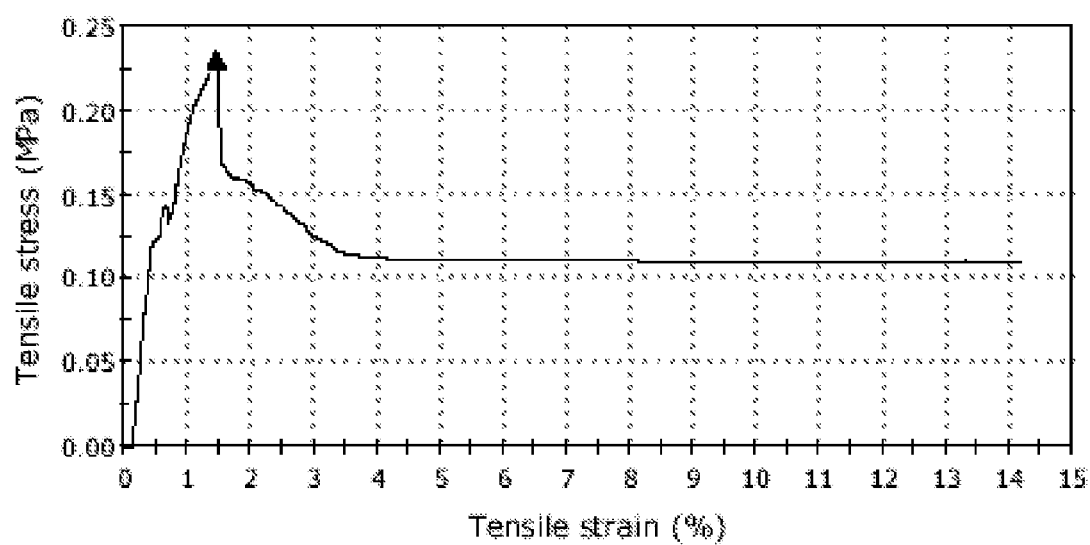
FIG. 13 is a representative curve showing co-injectable tissue adhesive strength of a sample Bioadhesive Hydrogel Composition.

This sample Bioadhesive Hydrogel Composition was more dilute than the Bioadhesive Hydrogel Composition described in Table 3, but also was designed to have a stoichiometric reaction between the aldehyde groups (on the dialdehyde) and an equivalent number of amine groups on the PEI. A thin layer (approximately 0.5 mm) of this sample Bioadhesive Hydrogel Composition was subjected to a tissue adhesion test in a butt joint configuration as described in the method of ASTM F2258-05. To test the tissue adhesive strength, pieces of porcine skin were attached to 2.5 cm square plates on an Instron Mechanical Testing System per ASTM F2258-05 and the layer of the Bioadhesive Hydrogel Composition was placed between the pieces of skin. Tissue adhesion for the Bioadhesive Hydrogel Composition was observed, in this case, to be as high as 120 kPa. A representative graph of the tissue adhesion test for the Bioadhesive Hydrogel Composition is depicted in FIG. 13. By comparison, a PVA/PEI Hydrogel Precursor Composition demonstrated a tissue adhesion of 98 kPa. This indicated that the aldehyde amine reaction between the glutaraldehyde and the tissue was enhancing the adhesion between the polymer and the tissue.

Example 9

Bioadhesive Hydrogel Compositions Containing Poly(Ethylene Glycol)Dialdehyde

Figure 14:
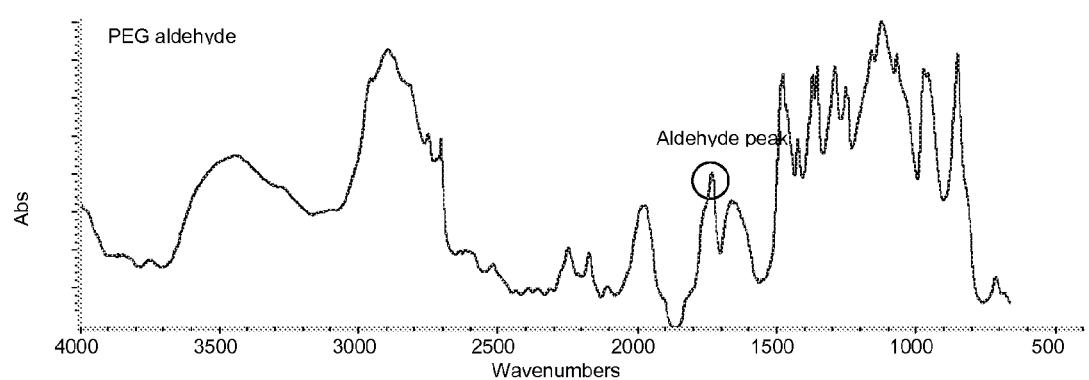
FIG. 14 is a FTIR spectrum analysis of PEG-dialdehyde.

A Bioadhesive Hydrogel Composition was prepared in the manner of Example 7 using a poly(ethylene glycol) dialdehyde (PEG-dialdehyde). FIG. 14 shows a FT-IR spectrum demonstrating the presence of the aldehyde group on the PEG polymer. The aldehyde groups on the PEG-dialdehyde will react with amine groups in the same way that smaller molecules containing aldehyde groups, such as, for example, glutaraldehyde, will. When PEG-dialdehyde is combined with a PVA/PEI mixture to form the Bioadhesive Hydrogel Composition, a similar color change to a reddish-orange was observed, demonstrating that the aldehyde/amine reaction had taken place.

The embodiments set forth above, among those made apparent from the preceding description, are efficiently attained and, since certain changes may be made in carrying out the above method of forming and in the resulting composition without departing from the spirit and scope of the invention, it is intended that all material contained in the above description shall be interpreted as illustrative and not in a limiting sense.

It will also be understood that the embodiments presented herein are intended to cover all of the generic and specific features of the composition herein described and all statements of the scope of the invention which, as a matter of language, might be said to fall therebetween. Particularly it is to be understood that in said embodiments, ingredients or compounds recited in the singular are intended to include compatible mixtures of such ingredients.

It will be appreciated by those skilled in the art that changes could be made to the embodiments described above without departing from the broad inventive concept thereof It is understood, therefore, that this invention is not limited to the particular embodiments disclosed, but is intended to cover modifications within the spirit and scope of the present invention as defined by the appended claims.

The invention claimed is:

1. A bioadhesive hydrogel composition for repairing or supplementing a nucleus pulposus of an intervertebral disc comprising at least a first component, a second component and a third component, the first component comprising an amine-containing polymer component at a concentration from about 0.1% weight by weight to about 13.65% weight by weight, the second component comprising a hydrophilic polymer or pre-polymer component comprising poly(vinyl alcohol) at a concentration from about 3% weight by weight to about 35% weight by weight, the third component comprising an aldehyde component at a concentration from about 0.1% weight by weight to about 30% weight by weight, wherein the first component, the second component and the third component are crosslinked.

2. The composition of claim 1, wherein the amine-containing polymer component is selected from the group consisting of poly(ethylene imine), poly(diethyl aminoethyl methacrylate), poly(ethyl aminoethyl methacrylate), amine-grafted poly(vinyl alcohol) or amine-containing poly(ethylene glycol).

3. The composition of claim 1, wherein the amine-containing polymer component is poly(ethylene imine).

4. The composition of claim 1, wherein the hydrophilic polymer or pre-polymer component is selected from the group consisting of poly(vinyl alcohol) and poly(ethylene glycol).

5. The composition of claim 1, wherein the hydrophilic polymer or pre-polymer component consists of poly(vinyl alcohol).

6. The composition of claim 1, wherein the aldehyde component is selected from the group consisting of glutaraldehyde, poly(ethylene glycol)-dialdehyde, glyoxal, formaldehyde and malonaldehyde.

7. The composition of claim 1, wherein the aldehyde component is glutaraldehyde.

8. The composition of claim 1, wherein the first component and the second component are crosslinked by a method selected from the group consisting of cryogelation, dehydration processing, radiation and exposure to chemicals.

9. The composition of claim 1, wherein the first, second and third components are injectable immediately after mixing but not after forty-eight hours.

10. The composition of claim 1, wherein the amine-containing polymer component and the aldehyde component are combined in such a way as to achieve about a one to one molar ratio of reactive amine groups to aldehyde groups.

11. The composition of claim 1, wherein the composition is pre-conditioned with an aqueous solution of poly(ethylene imine).

12. The composition of claim 1, wherein the amine-containing polymer component is poly(ethylene imine) at a concentration from about 5% weight by weight to about 11% weight by weight, the hydrophilic polymer or pre-polymer component is poly(vinyl alcohol) at a concentration from about 4% weight by weight to about 15% weight by weight and the aldehyde component is at a concentration from about 2% weight by weight to about 7% weight by weight.

13. A bioadhesive hydrogel composition for repairing or supplementing a nucleus pulposus of an intervertebral disc comprising at least a first component, a second component and a third component, the first component comprising an amine-containing polymer component at a concentration from about 5% weight by weight to about 11% weight by weight, the second component comprising a hydrophilic polymer or pre-polymer component comprising poly(vinyl alcohol) at a concentration from about 4% weight by weight to about 15% weight by weight, the third component comprising an aldehyde component at a concentration from about 2% weight by weight to about 7% weight by weight, wherein the first component, the second component and the third component are crosslinked and the amine-containing polymer component and the aldehyde component are combined in such a way as to achieve about a one to one molar ratio of reactive amine groups to aldehyde groups.

14. A kit for forming a bioadhesive hydrogel composition comprising:
at least one first container containing an amine-containing polymer component at a sufficient concentration to be injectable at room temperature or under operating room conditions;
at least one second container containing a hydrophilic polymer or pre-polymer component comprising poly(vinyl alcohol) at a sufficient concentration to be injectable at room temperature or under operating room conditions; and
at least one third container containing an aldehyde component at a sufficient concentration to be injectable at room temperature or under operating room conditions,
wherein when the aldehyde component, the amine-containing polymer component and the hydrophilic polymer or pre-polymer component are mixed the composition is crosslinked and contains about 0.1% weight by weight to about 13.65% weight by weight of the amine-containing component, about 3% weight by weight to about 35% weight by weight of hydrophilic polymer or pre-polymer component and about 0.1% weight by weight to about 30% weight by weight of aldehyde component.

15. A kit for forming a bioadhesive hydrogel composition comprising:

at least one first container containing a precursor composition comprising an amine-containing polymer component crosslinked to a hydrophilic polymer or pre-polymer component comprising poly(vinyl alcohol); and at least one second container loaded with an aldehyde component at a sufficient concentration to be injectable at room temperature or under operating room conditions, wherein when the aldehyde component, the amine-containing polymer component and the hydrophilic polymer or pre-polymer component are mixed the composition is crosslinked and contains about 0.1% weight by weight to about 13.65% weight by weight of the amine-containing component, about 3% weight by weight to about 35% weight by weight of hydrophilic polymer or pre-polymer component and about 0.1% weight by weight to about 30% weight by weight of aldehyde component.

16. The kit of claim 15, wherein the precursor composition is a hydrogel.

17. The kit of claim 15, wherein the precursor composition is injectable at room temperature or under operating room conditions.

18. A method of repairing or supplementing a nucleus pulposus of an intervertebral disc comprising:

providing a bioadhesive hydrogel composition comprising at least a first component, a second component and a third component, the first component comprising an amine-containing polymer component at a concentration from about 0.1% weight by weight to about 13.65% weight by weight, the second component comprising a hydrophilic polymer or pre-polymer component comprising poly(vinyl alcohol) at a concentration from about 3% weight by weight to about 35% weight by weight, the third component comprising an aldehyde component at a concentration from about 0.1% weight by weight to about 30% weight by weight, wherein the first component, the second component and the third component are crosslinked; and implanting the composition into a patient.

19. The method of claim 18, wherein the bioadhesive hydrogel composition is implanted in the patient via injection.

20. The method of claim 18, wherein the bioadhesive hydrogel composition solidifies in situ.

21. The method of claim 18, wherein the bioadhesive hydrogel composition is implanted in the patient by inserting a solidified composition into the patient.

22. The method of claim 18, wherein the composition is pre-conditioned with an aqueous solution of poly (ethylene imine) before implantation into the patient.

23. The method of claim 18, wherein the amine-containing polymer component and the aldehyde component are combined in such a way as to achieve about a one to one molar ratio of reactive amine groups to aldehyde groups.

* * * * *